United States Patent [19]

Burns et al.

[11] 4,118,286
[45] Oct. 3, 1978

[54] PROCESS FOR REDUCING THE ACIDITY OF ORGANIC POLYMERIC ISOCYANATES

[75] Inventors: Simon Pierce Burns; John Monte Walton, both of Austin, Tex.

[73] Assignee: Texaco Development Corp., New York, N.Y.

[21] Appl. No.: 508,984

[22] Filed: Sep. 25, 1974

[51] Int. Cl.$^2$ .............................................. B01D 3/00
[52] U.S. Cl. ................................ 203/89; 260/453 SP; 203/98; 203/69
[58] Field of Search ............................ 203/98, 89, 69; 260/453 SP

[56] References Cited

U.S. PATENT DOCUMENTS

| | | | |
|---|---|---|---|
| 3,219,678 | 11/1965 | Kober et al. | 260/453 SP |
| 3,793,362 | 2/1974 | Kalakowski et al. | 260/453 SP |
| 3,853,936 | 12/1974 | Van Winkle | 203/89 X |

Primary Examiner—James H. Tayman, Jr.
Attorney, Agent, or Firm—James L. Bailey

[57] ABSTRACT

In a process for purifying and reducing the acidity of a polymethylene polyphenylpolyisocyanate mixture wherein the mixture is subjected to a distillation step, such as by passing a flowing stream of a crude polymethylene polyphenylpolyisocyanate mixture through a distillation column which has a reboiler means consisting of a thin film evaporator apparatus mounted therewith for rapidly heating the stream to about 190° C. to about 250° C. whereby the solvent and impurities are taken overhead, and then allowing the distillation residue of polymethylene polyphenylpolyisocyanate to cool, an improvement is disclosed which comprises maintaining the distillation residue of the polymethylene polyphenylpolyisocyanate at a temperature of about 190° C. to about 250° C. for a time period of from about 1 to about 60 minutes and then recirculating continuously a portion of the distillation residue to the distillation column for admixture with the flowing feed stream of crude polymethylene polyphenylpolyisocyanate at a recirculation rate of from about 1:1 to about 3:1 volumes of isocyanate distillation residue per volume of crude isocyanate feed. The acid level of the polymethylene polyphenylpolyisocyanate mixture treated by the improved process of the invention is substantially reduced without adversely affecting the isocyanate equivalent weight, viscosity or other physical and chemical characteristics of the product.

4 Claims, 1 Drawing Figure

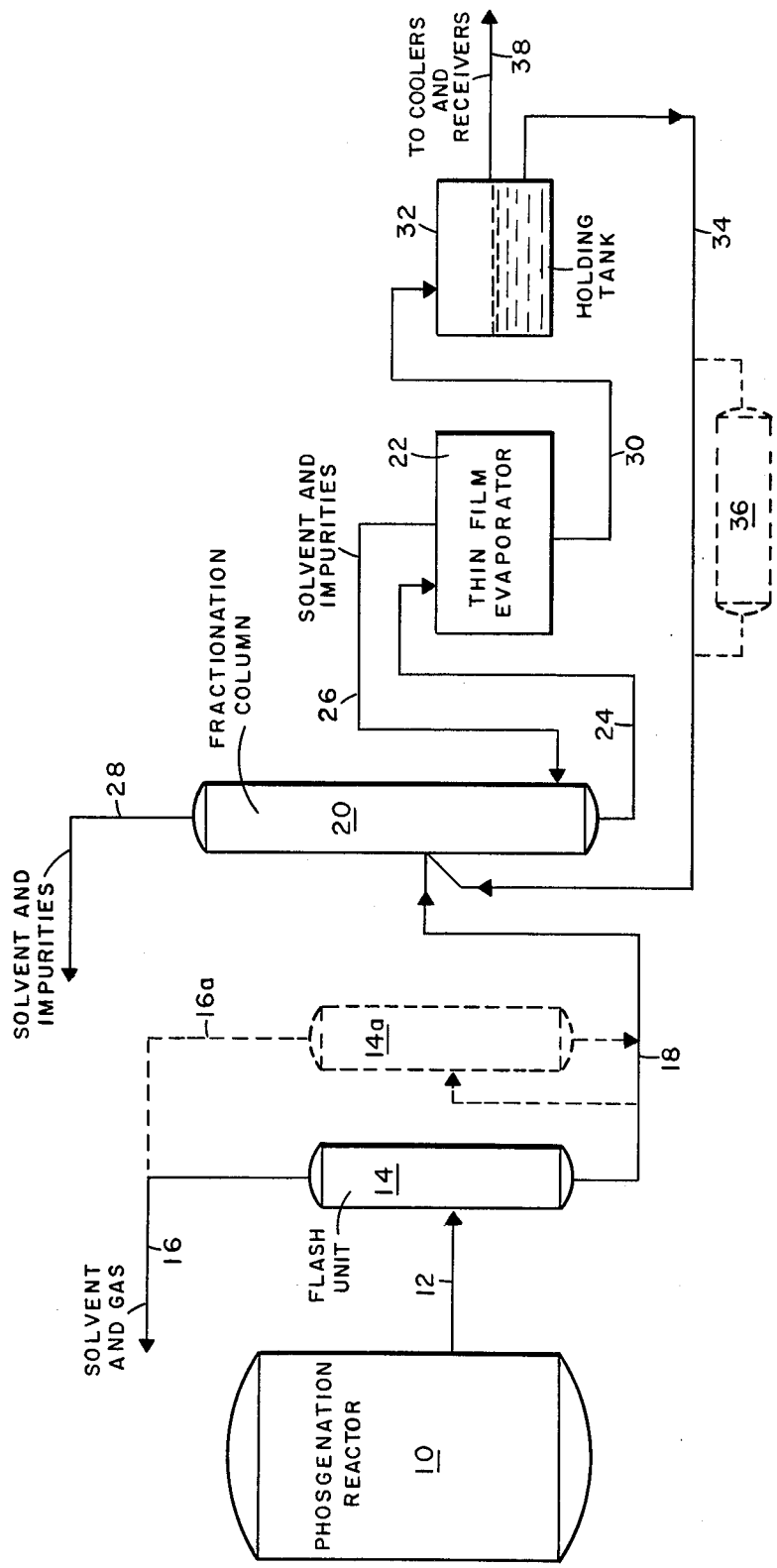

PROCESS FOR REDUCING THE ACIDITY OF ORGANIC POLYMERIC ISOCYANATES

BACKGROUND OF THE INVENTION

1. Field of the Invention

This invention relates to organic polymeric isocyanates and more particularly pertains to an improved process for purifying and reducing the acidity in methylene-bridged polyphenylpolyisocyanate mixtures.

2. Description of the Prior Art

Organic isocyanates are generally prepared by the phosgenation of corresponding amine compounds by one of the many well-known phosgenation processes. These phosgenation processes usually result in crude isocyanate products that contain residual acidic materials which adversely affect the reactivity of the isocyanate. The acidic material contaminants are generally those which respond as acids in standard analytical tests known and employed in the art. The acidic material contaminants are known to include hydrogen chloride and a variety of unknown by-product materials of which only some appear to be hydrogen chloride precursors. These materials also respond as acids in the aforementioned standard analytical tests.

There are procedures known for purifying organic isocyanates to reduce acidity levels and otherwise increase their reactivity rates. Generally, the most common practice in the industry is to subject crude isocyanate mixtures to one or more distillation steps, such as by passing a stream of the crude reaction mixture of the phosgenation reaction mentioned hereinabove, which contains the organic isocyanate, solvent and impurities, through one or more distillation columns whereby the solvent employed in the phosgenation reaction and acidic material contaminants are carried overhead, leaving the organic isocyanate as residue. For example, U.S. Pat. No. 3,264,336 discloses the employment of fractional distillation as a method for removing acid contaminants from organic isocyanates.

However, conventional distillation techniques have left much to be desired in regard to reducing the acidity levels of organic isocyanates. Apparently, it is difficult to separate many acidic material contaminants from the isocyanate material by conventional distillation.

There are several procedures described in the literature for improving the separation of acidic material and other contaminants from isocyanates by distillation. For example, a number of methods have been described which comprise treatment of crude organic isocyanates with metals, such as copper, silver, nickel, iron, zinc, cobalt, aluminum, bismuth, and the like, and then distilling the mixtures for separation. It is disclosed that the metallic compounds form materials or complexes with acidic material contaminants of the crude isocyanate which can be readily separated by distillation, thereby resulting in an isocyanate having reduced acidity. See U.S. Pat. No. 3,155,699, 3,264,336, 3,373,182 and 3,458,558.

In addition, U.S. Pat. No. 3,219,678 discloses a process for purifying organic isocyanates for the reduction of the hydrolyzable chloride content therein which includes the steps of subjecting a crude organic isocyanate mixture that has been previously degassed and subjected to distillation for solvent removal (employed in the aforementioned conventional phosgenation procedure) to a temperature considerably above those temperatures required and used in conventional degassing procedures for the cleavage of organic carbamyl chlorides formed in the phosgenation reaction into organic isocyanate and hydrogen chloride, for extended periods of time, and then distilling the mixture to separate the organic isocyanate. It is disclosed that the heating prior to distillation apparently removes hydrolyzable chloride contaminants or those responsible for hydrolyzable chloride content which are not removed by simple distillation of the organic isocyanate. However, the process disclosed in U.S. Pat. No. 3,219,678 leaves much to be desired from a commercial operation standpoint inasmuch as it would apparently require the utilization of a plurality of distillation columns and/or extensive tie-up of plant production equipment which necessarily reduce the economics of the process.

Furthermore, the above-mentioned procedures have especially left much to be desired for purifying and reducing the acidity levels of polymethylene polyphenylpolyisocyanate mixtures. Generally, polymethylene polyphenylpolyisocyanate mixtures are prepared by the well-known procedures of mixing and reacting phosgene, in the presence of a compatible solvent such as monochlorobenzene, with a corresponding methylene-bridged polyphenyl polyamine mixture prepared by the condensation reaction of formaldehyde and aniline or a related polyamine in the presence of a strong mineral acid or alumina-silica catalyst. Illustrative methods of the preparation of methylene-bridged polyphenyl polyamines and corresponding polymethylene polyphenylpolyisocyanates are described in U.S. Pat. Nos. 2,683,730; 2,950,263; 3,012,008; 3,344,162; and 3,362,979, to name a few. The primary disadvantage of employing the above-mentioned processes for purifying and reducing the acidity of polymethylene polyphenylpolyisocyanates is the fact that these materials are heat-sensitive. Exposure to high temperatures for extended time periods adversely affect the chemical and physical properties of polymethylene polyphenylpolyisocyanate mixtures, such as viscosity, isocyanate equivalent weight, weight percent free isocyanate, and the like. Furthermore, polymethylene polyphenylpolyisocyanates prepared by the aforementioned processes exist as mixtures of methylene diphenylisocyanate and higher functionality, higher molecular weight methylene-bridged polyphenylpolyisocyanates which have variable boiling points.

For these reasons, it has heretofore been a common practice in the industry to purify and reduce the acidity of polymethylene polyphenylpolyisocyanate mixtures by a distillation procedure employing a fractional distillation column having a reboiler consisting of a thin film evaporator means. More particularly, in accordance with conventional techniques, a crude polymethylene polyphenylpolyisocyanate mixture, from the phosgenation reaction containing solvent and impurities is initially degassed by rapidly heating the crude mixture to about 70° to about 90° C., under about 60 to about 90 mm. Hg absolute pressure, to remove unreacted phosgene and other highly volatile impurities, and then passed through the fractional distillation column and thin film evaporator means where the mixture is subjected to high temperature for only a few seconds to reduce acidity without significantly affecting the polymethylene polyphenylpolyisocyanate mixture physical and chemical characteristics. The solvent and impurities are taken overhead.

Although the distillation procedure described immediately hereinabove has been found to be effective in removing the solvent and high volatile impurities from the polymethylene polyphenylpolyisocyanate mixtures without adversely affecting the physical and chemical properties of the mixture, it has left much to be desired in regard to reducing the acidity of the isocyanate product.

Accordingly, it is the primary object of the present invention to provide an improved process for treating a polymethylene polyphenylpolyisocyanate mixture whereby the resulting isocyanate has a reduced acid level without adversely affecting the viscosity, isocyanate equivalent weight, isocyanate reactivity and like physical and chemical characteristics.

It is another object of the present invention to provide an improvement in the process for purifying and reducing the acidity level of a polymethylene polyphenylpolyisocyanate subjected to a distillation step for separation of the solvent employed in a conventional phosgenation reaction and other contaminants.

It is yet another object of the present invention to provide an improvement in the process for purifying and reducing the acidity of polymethylene polyphenylpolyisocyanate mixture subjected to distillation procedures which does not require the employment of an extensive series of distillation columns and related apparatus and/or extensive tie-up of plant equipment and related long time requirements.

Other objects and advantages of the present invention will become readily apparent to those having ordinary skill in the art from the following description of the invention along with the attached drawing.

SUMMARY OF THE INVENTION

The present invention is an improvement in the process for purifying and reducing the acidity level of a polymethylene polyphenylpolyisocyanate mixture prepared by the phosgenation of the corresponding methylene-bridged polyphenylpolyamine mixture wherein the crude phosgenated reaction product, after being subjected to conventional degassing procedures, is subjected to at least one distillation step to remove excess solvent and impurities therefrom, such as by passing a flowing feed stream of the degassed crude phosgenated mixture through a distillation column having a thin film evaporator means mounted therewith for heating the mixture to from about 190° C. to about 250° C., taking the excess solvent and impurities overhead from the distillation column, and then allowing the resulting polymethylene polyphenylpolyisocyanate product residue from the distillation column and evaporator means to cool. The improvement of the invention comprises maintaining the polymethylene polyphenylpolyisocyanate product residue from the distillation column and evaporator means at a temperature of from about 190° C. to about 250° C. for about 1 to 60 minutes, such as by holding in a temperature controlled holding tank, and recirculating continuously a portion of the product residue being maintained at that temperature to the distillation column for admixture with the flowing feed stream of crude polymethylene polyphenylpolyisocyanate mixture. It has been found that the maintaining and holding of the polymethylene polyphenylpolyisocyanate product residue at temperatures within the above-mentioned range for the described times in combination with the continuous recirculation of a portion thereof for admixture with the crude feed stream in the distillation column results in a substantial reduction in the acid level of product mixture without adversely affecting the isocyanate equivalent weight, viscosity and other physical and chemical properties of the product. Moreover, the reduction of acidity of polymethylene polyphenylpolyisocyanate mixtures treated by the process of the invention is obtained without the use of a plurality of distillation steps heretofore usually required, thereby eliminating the necessity of employing extensive distillation equipment and/or extended process time requirements. The process of the invention is especially effective for reducing the acidity of methylene-bridged polyphenylpolyisocyanate mixtures prepared by the aforementioned procedures which are known to be extremely heat-sensitive and thus adversely affected by the extensive distillation procedures heretofore employed for removing impurities from crude organic isocyanate products.

DESCRIPTION OF THE DRAWING

The detailed description of our invention, which follows herein, will be further illustrated in connection with the attached drawing, which is a schematic flow sheet illustrating a preferred embodiment of the invention. In order to simplify the drawing, conventional details, such as valves, pumps, condensers, reboilers, flow and temperature control devices, and the like, have not been shown since the construction, operation and function thereof is known to those of ordinary skill in the art.

DETAILED DESCRIPTION OF THE INVENTION

As hereinbefore mentioned, the process of the invention is particularly useful for purifying and reducing the acidity of polymethylene polyphenylpolyisocyanate mixtures. Any polymethylene polyphenylpolyisocyanate mixture, prepared by any process known in the art can be treated by the invention process. Inasmuch as polymethylene polyphenylpolyisocyanate mixtures are well-known, and methods for their preparation and the methods for the preparation of the corresponding methylene-bridged polyphenylpolyamine mixtures employed for their preparation are well-known, as shown by the above-noted patents, further detailed description thereof will not be set forth herein.

Thus, for the purposes of brevity only, the term "polymethylene polyphenylpolyisocyanate mixture" will hereafter be referred to as the isocyanate mixture or product.

Referring now to the drawing, in accordance with the process of the present invention, a crude isocyanate feed stream, obtained from any of the aforementioned phosgenation processes of corresponding methylene-bridged polyphenyl polyamines and which contain the isocyanate, a compatible organic liquid solvent, such as monochlorobenzene, and impurities, is fed from the phosgenation reactor 10 through line 12 through one or more flashing units 14,14a (in phantom) wherein the feed stream is heated at a temperature of from about 70° to about 90° C. at about 60 to about 90 mm. Hg absolute pressure for about 15 minutes to about 2 hours. As the isocyanate feed stream passes through the flashing units 14,14a, unreacted phosgene, some solvent and some high volatile impurities are taken overhead through line 16,16a (in phantom). The liquid bottoms from the flash units 14,14a, i.e., the degassed isocyanate feed stream, then moves through line 18 and is fed to the fractionation distillation column 20, preferably at about midpoint of the column 20. The fractionation column 20 is mounted with a reboiler means consisting of a thin film evaporator 22. The thin film evaporator 22 is mounted to the fractionation column by any conventional means, such as by lines 24 and 26. For example, the isocyanate feed stream passes through the fractionation column 20 and line 24 to the thin film evaporator 22 wherein it is heated to a temperature of from about 190°–250° C. for only a few seconds. The solvent and other impurities volatilized in the thin film evaporator 22 are then passed through line 26 back to the bottom of the fractionation column 20, passing countercurrent to the feed stream, and are taken overhead through line 28 for reuse or discard. The volatilized solvent and impurities are preferably taken overhead from the thin film evaporator at a temperature of about 110° C. to about 215° C. and passed through the fractionation column 20 whereby the isocyanate feed stream flowing countercurrently therewith is heated so as to provide a temperature of about 50°–80° C. at the fractionator column 20 midpoint and an overhead temperature of about 30°–50° C., depending upon the particular solvent employed during the aforementioned phosgenation reaction. In addition, the fractionation column 20 is preferably operated under a pressure of from about atmospheric to about 15 mm. Hg absolute and includes reflux condenser means (not shown) to provide reflux ratios of from about 0.5:1 to about 5:1 to prevent excessive loss of the isocyanate products.

In accordance with the process of the present invention, the isocyanate product residue or bottoms from the thin film evaporator 22 is then removed therefrom through line 30 to a holding tank 32 wherein the residue is maintained at a temperature of from about 190° C. to about 250° C., i.e., essentially the same temperature as heated to in the thin film evaporator 22, for a time period of from about 1 to about 60 minutes. The temperature can be maintained in the holding tank 32 by any conventional means, such as by equipping the holding tank 32 with appropriate insulation and/or additional heating means. The desired holding time can be provided by any conventional means such as by equipping the holding tank 2 with appropriate product removal means for continuously removing portions of the heated isocyanate product from the holding tank 32 when it collects and reaches a certain level. Preferably, the isocyanate product residue is maintained at a temperature of from about 210° C. to about 240° C. for about 1 to about 15 minutes. It has been determined that, as higher temperatures are employed, lower holding times are required.

A portion of the isocyanate product is removed continuously from the holding tank through line 34 and continuously recirculated back to the fractionation column 20 at its mid-point for intimate admixture with the crude isocyanate feed stream entering the fractionation column 20 through line 18 from the flash unit 14,14a. Most unexpectedly, it has been found that the continuous recirculation of the isocyanate product residue from the thin film evaporator 22 which has been maintained at the aforesaid temperature for the aforesaid time at recirculation volume ratios of from about 1:1 to as high as 3:1, temperature-maintained product residue:crude flashed feed product, results in drastic reduction of the acid content of the polymethylene polyphenylpolyisocyanate mixture being treated, as further shown in the examples set forth hereafter. Preferably, a recirculation rate of from about 2 to about 3 volumes recirculated product per volume of crude feed is employed.

The isocyanate product residue or evaporator bottoms recirculated through line 34 can be recirculated at the same temperature maintained in the holding tank 32 if desired. However, the product residue can be recirculated at temperatures as low as about 25° C., such as by passing the recirculated residue through a cooling tank 36 (in phantom) without adverse results so as to reduce potential equipment maintenance problems.

The isocyanate residue product is also removed from the holding tank 32 through line 38, which can include the above-mentioned product removal means (not shown). The product removal means can comprise a nozzle having an orifice of desired size to provide the desired removal rate and holding time. It can be readily appreciated that the volume of product removed through line 38 is preferably substantially the same as the volume of crude isocyanate feed fed to the fractionation column 20 through line 18 to provide processing equilibrium. The removed product is then passed through conventional cooling means to storage receivers, both not shown.

The invention will be further illustrated by the following specific examples which are given by way of illustration and not as limitations on the scope of this invention.

All of the following examples were carried out in a fractional distillation column which consisted of a 4-inch column packed with Intalox Saddles (Norton Company, Akron, Ohio). A reboiler was mounted with the column which consisted of a thin film evaporator which had a heat transfer surface of 1.4 sq. ft. The column also had a three-way valve means activated by a timer mounted therewith to provide the desired reflux, along with pressure means. A double-pipe heat exchanger was attached by appropriate conduits to the head of the column to condense vapors taken overhead. The crude isocyanate feed mixture to be treated, previously degassed, was introduced through a conduit connected at the mid-point of the column. For heat treatment, a small tank was attached to the bottom of the evaporator. The heated isocyanate product residue from the bottom of the heat exchanger entered the tank through a dip-tube mounted therein, filled the tank to a level needed to give the desired holding time, and overflowed through a nozzle and then through a cooler to receivers. Holding time in the tank was adjusted by selecting one of multiple nozzles provided on the side of the tank. The tank was wrapped with a coil of tubing through which hot oil flowed to maintain a constant temperature in the isocyanate product residue, and the entire tank was insulated to prevent heat loss. Recirculating means were provided for recirculating a portion of the product held in the holding tank back to the mid-point of the column for admixture with the fresh crude isocyanate feed. The recirculating means included appropriate conduits and metering devices attached respectively to the holding tank and distillation column at mid-point for removing the isocyanate product residue from the holding tank to the distillation column mid-point. The recirculating means included a cooling tank mounted with the conduit for reducing the temperature thereof to about 50° C. to reduce metering device maintenance. The thin film evaporator also had appropriate conduits mounted therewith for passing the isocyanate product residue directly therefrom to the cooler and receivers bypassing the holding tank. This bypass means and the recirculating means both had cutoff valves for operation when desired.

The various data relating to acid levels in the following examples were obtained as follows.

Acidity Determination 1.2 to 1.4 g. of the isocyanate mixture to be analyzed is weighed, to the nearest 0.1 mg., into each of two 250-ml. beakers. 50 ml. of methanol and then 50 ml. of toluene are pipetted into each beaker. A stirring bar is added to each beaker which are then placed on a preheated (maximum heat) stirrer hotplate. Thermometers are placed in each solution and the solutions are heated to 60° C. in less than 3 minutes. The beakers are then removed from the hotplate, covered with watch glasses and allowed to stand for one hour, plus or minus 5 minutes. With a pipette, the thermometers and the walls of each beaker are washed down with 10 ml. methanol. Using a pH meter with glass and calomel electrode, each solution is then titrated with 0.02N methanolic sodium hydroxide, to pH 7. The acidity, determined as HCl, is then calculated according to the following formula:

$$\text{Wt. \% Acid (Basis HCl)} = \frac{\text{(ml. of NaOH) (N of NaOH) (3.646)}}{\text{grams of sample}}$$

EXAMPLE I

A crude reaction mixture resulting from the phosgenation of a polymethylene polyphenylpolyamine mixture from the condensation reaction of aniline and formaldehyde, containing 20–25 wt.% monochlorobenzene and 75–80 wt.% polymethylene polyphenylpolyisocyanate mixture, previously flashed at about 70° C. to about 90° C. at about 60 to 90 mm. Hg absolute pressure, was fed to the distillation column described hereinabove which was adjusted to provide holding of the isocyanate product residue in the holding tank and recirculating a portion therefrom. The crude flashed mixture was fed to the distillation column at a feed rate of 8.3 lbs./hr. The distillation column was operated under 15 mm. Hg absolute pressure and a reflux ratio of 2/1. The holding tank was adjusted with appropriate nozzles for a holding time of 1.5 minutes. The recirculating means was adjusted to provide a recirculation rate of 20.7 lbs./hr. Temperatures were recorded at various points as follows:

| Point | Temperature Range |
|---|---|
| Column head | 27–32° C. |
| Column mid-point | 57–81° C. |
| Vapor from evaporator | 126–212° C. |
| Product from evaporator | 200–229° C. |
| Holding tank | 216–225° C. |

A portion of the product was removed from the holding tank at a rate of 8.3 lbs./hr. and passed through the cooler to receivers. A portion of the product was removed from a receiver and analyzed, the results of which are set forth in the following Table 1.

TABLE 1

| | Product Analysis |
|---|---|
| Acidity, wt. % as HCl | 0.054 |
| Isocyanate content, meq/g | 7.42 |
| Viscosity, cp. 25° C. | 285 |
| MDI content, wt. % | 43.5 |
| 4,4′-isomer, wt. % of MDI | 75.7 |

EXAMPLE II

A crude reaction mixture of about 50 wt.% monochlorobenzene and 50 wt.% polymethylene polyphenylpolyisocyanate, obtained from the phosgenation of a polymethylene polyphenylpolyamine mixture prepared by the condensation reaction of aniline and formaldehyde which had been previously degassed by passing through a flash unit operated at about 70° C. to about 90° C. at 60 to 90 mm. Hg absolute pressure, was fed to the distillation column described hereinabove at a feed rate of 31.6 lbs./hr. The crude reaction feed mixture was the same as described in Example I except for the wt.% monochlorobenzene present. The distillation column apparatus described hereinabove was adjusted so as to pass the treated isocyanate product residue from the evaporator directly through the cooler to receivers bypassing the holding tank and recirculating means. The distillation column was operated under 15 mm. Hg absolute pressure and a reflux ratio of 2/1. Temperatures, measured at various points, were as follows:

| Point | Temperature Range |
|---|---|
| Column head | 32–47° C. |
| Column mid-point | 53–61° C. |
| Vapor from evaporator | 111–215° C. |
| Product from evaporator | 230–242° C. |

A portion of the isocyanate product residue from a receiver was analyzed, the results being set forth in the following Table 2.

TABLE 2

| | Product Analysis |
|---|---|
| Acidity, wt. % as HCl | 0.20 |
| Isocyanate content, meq/g | 7.60 |
| Viscosity, cp. at 25° C. | 160 |
| MDI content, wt. % | 45.7 |
| 4,4′-isomer, wt. % of MDI | 76.6 |

A comparison of the results of Table 2 to those of Table 1 illustrates the improvement in reduction of acidity of organic polyisocyanate mixtures treated in accordance with the process of the invention over a conventional distillation technique.

EXAMPLE III

The crude flashed reaction feed mixture described in Example II was fed to the distillation column described hereinabove at a feed rate of 27.4 lbs./hr. The distillation column was adjusted so that the isocyanate product residue from the evaporator would be removed to the holding tank which was adjusted to maintain the temperature of the product residue at about 172°–219° C. for about 11 minutes holding time. The distillation column was operated under 15 mm. Hg absolute pressure and a reflux ratio of 2/1. Temperatures were recorded at various points as follows:

| Point | Temperature Range |
|---|---|
| Column head | 31–33° C. |
| Column mid-point | 58–76° C. |
| Vapor from evaporator | 150–199° C. |
| Product from evaporator | — |
| Holding tank | 172–219° C. |

The product passed from the holding tank at the feed rate through a cooler to receivers. A portion of the treated isocyanate residue product was then analyzed, the results of which are set forth in the following Table 3.

TABLE 3

|  | Product Analysis |
| --- | --- |
| Acidity, wt. % as HCl | 0.15 |
| Isocyanate content, meq/g | 7.59 |
| Viscosity, cp. at 25° C. | 174 |
| MDI content, wt. % | 47.5 |
| 4,4'-isomer, wt. % of MDI | 76.0 |

A comparison of the results set forth in Table 3 with the results of Table 2 shows that holding the mixture at the elevated temperature provides improved acidity reduction over conventional distillation. However, a comparison of the results of the table with those of Table 1 illustrates the unexpected improvement of acidity reduction by recirculating a portion of the isocyanate product residue in accordance with the present invention.

EXAMPLE IV

A crude reaction mixture resulting from the phosgenation of a polymethylene polyphenylpolyamine mixture of the condensation reaction of aniline and formaldehyde, containing 20-25 wt.% monochlorobenzene and 75-80 wt.% of the polymethylene polyphenylpolyisocyanate mixture, which had been previously flashed by passing through a flash unit operated at about 70° C. to about 90° C. at 60-90 mm. Hg absolute pressure, was fed to the distillation column described hereinabove. The distillation column was adjusted as described in Example I to provide holding of the isocyanate product residue in the holding tank and recirculating a portion therefrom back to the distillation column. The crude flashed mixture was fed to the distillation column at a feed rate of 7.0 lbs. per hour and the distillation column was operated under 15 mm. Hg absolute pressure and a reflux ratio of 2/1. The holding tank was adjusted with appropriate nozzles for a holding time of 1.5 minutes and the recirculating means was adjusted to provide a recirculation rate of 23.0 lbs./hour. During operation, temperatures were recorded at various points as follows:

| Point | Temperature Range |
| --- | --- |
| Column head | 23-27° C. |
| Column mid-point | 58-77° C. |
| Vapor from evaporator | 173-200° C. |
| Product from evaporator | 174-190° C. |
| Holding tank | 194-209° C. |

A portion of the product was removed from the holding tank at the feed rate of 7.0 lbs./hour and passed through the cooler to receivers. Analysis of a portion of the product removed from a receiver provided the following results set forth in Table 4:

TABLE 4

|  | Product Analysis |
| --- | --- |
| Acidity, wt. % as HCl | 0.068 |
| Isocyanate content, meq/g | 7.47 |
| Viscosity, cp. at 25° C. | 80 |
| MDI content, wt. % | 66.2 |
| 4,4 40 -isomer, wt. % of MDI | 75.8 |

A comparison of the results of Table 4 to those set forth in Tables 2 and 3 further illustrate the improved reduction of acid content in polymethylene polyphenylpolyisocyanate mixtures treated in accordance with the present invention.

From the foregoing description and examples of this invention, those of ordinary skill in the art may make many modifications and variations therefrom without departing from the scope of the invention as hereinafter claimed.

We claim:

1. In a process for purifying and reducing the acidity of a polymethylene polyphenylpolyisocyanate mixture comprising distilling, in a distillation step, a crude polymethylene polyphenylpolyisocyanate mixture resulting from the phosgenation of a corresponding polymethylene polyphenylpolyamine mixture in a solvent to remove the solvent and impurities therefrom, said distillation step being conducted by passing a flowing feed stream of the crude polymethylene polyphenylpolyisocyanate mixture through a distillation column having a thin film evaporator means mounted therewith for heating said mixture to a temperature of from about 190° C. to about 250° C., taking excess solvent and impurities overhead from the column, and then allowing the resulting polymethylene polyphenylpolyisocyanate distillation residue from the column and evaporator means to cool, the improvement which comprises:

maintaining the polymethylene polyphenylpolyisocyanate residue from the column and evaporator means at a temperature of from about 190° C. to about 250° C. for about 1 to about 60 minutes; and recirculating continuously a portion of said residue being maintained at said temperature for said time to said distillation column for admixture with said flowing feed stream of crude polymethylene polyphenylpolyisocyanate mixture, whereby the acidity content of the polymethylene polyphenylpolyisocyanate mixture is substantially reduced.

2. The process of claim 1 wherein the polymethylene polyphenylpolyisocyanate distillation residue maintained at about 190° C. to about 250° C. for about 1 to about 60 minutes is recirculated to said distillation column at a ratio of from about 1 to about 3 volumes of recirculated residue per volume of said crude polymethylene polyphenylpolyisocyanate feed stream.

3. The process in accordance with claim 1 wherein said polymethylene polyphenylpolyisocyanate residue is maintained at a temperature of from about 190° C. to about 225° C. for about 1 to about 15 minutes.

4. The process in accordance with claim 3, wherein said polymethylene polyphenylpolyisocyanate residue maintained at said temperature for said time is recirculated to said distillation column at a rate of about 2 to about 3 volumes maintained residue per volume of crude polymethylene polyphenylpolyisocyanate feed.

* * * * *